United States Patent
Edwards et al.

(10) Patent No.: US 9,375,221 B2
(45) Date of Patent: Jun. 28, 2016

(54) ORTHOPAEDIC CUTTING BLOCK HAVING A CHEMICALLY ETCHED METAL INSERT

(75) Inventors: Jon M. Edwards, Warsaw, IN (US); Henri G. Asselin, Jr., Lowell, MA (US); Todd R. Beaupre, Reading, MA (US); Donald E. Welling, Amesbury, MA (US); Roger J. White, Lexington, MA (US)

(73) Assignee: DEPUY (IRELAND), Cork (IE)

( * ) Notice: Subject to any disclaimer, the term of this patent is extended or adjusted under 35 U.S.C. 154(b) by 2185 days.

(21) Appl. No.: 12/345,118

(22) Filed: Dec. 29, 2008

(65) Prior Publication Data

US 2010/0168753 A1    Jul. 1, 2010

(51) Int. Cl.
*A61B 17/15* (2006.01)
*A61B 17/16* (2006.01)
*A61B 17/17* (2006.01)
*A61B 17/00* (2006.01)

(52) U.S. Cl.
CPC ........... *A61B 17/1659* (2013.01); *A61B 17/155* (2013.01); *A61B 17/157* (2013.01); *A61B 17/1675* (2013.01); *A61B 17/152* (2013.01); *A61B 17/1615* (2013.01); *A61B 17/1764* (2013.01); *A61B 2017/00526* (2013.01)

(58) Field of Classification Search
CPC ............... A61B 17/155; A61B 17/157; A61B 17/1659; A61B 17/152; A61B 2017/00526; A61B 2560/04; A61B 2560/0456; A61B 2560/0443
USPC ..................................... 606/87–89
See application file for complete search history.

(56) References Cited

U.S. PATENT DOCUMENTS

| | | | |
|---|---|---|---|
| 4,048,765 A * | 9/1977 | Samuelson ............ | 451/59 |
| 4,177,525 A * | 12/1979 | Arbogast et al. ............ | 623/55 |
| 5,053,037 A | 10/1991 | Lackey | |
| 5,100,408 A | 3/1992 | Lackey | |
| 5,282,803 A | 2/1994 | Lackey | |
| 5,415,662 A * | 5/1995 | Ferrante et al. ............ | 606/86 R |
| 5,415,663 A | 5/1995 | Luckman et al. | |

(Continued)

FOREIGN PATENT DOCUMENTS

EP    1 611 854 A1    1/2006
EP    1 967 143 A2    5/2008

(Continued)

OTHER PUBLICATIONS

Extended European Search Report for European Patent Application No. 11150573.1-2310, Mar. 25, 2011, 6 pgs.

(Continued)

*Primary Examiner* — Paul Prebilic
(74) *Attorney, Agent, or Firm* — Barnes & Thornburg LLP

(57) ABSTRACT

An orthopaedic surgical instrument comprising an orthopaedic cutting block includes a metallic bearing insert configured to support a bone cutting tool and a body molded to the bearing insert. The bearing insert includes a plurality of chemically etched holes, and the body is molded to the bearing insert such that each of the plurality of chemically etched holes is at least partially filled by a portion of the body. The body of the orthopaedic cutting block may include a bone-facing surface adapted to contact a portion of a patient's bone, and the bearing insert may be positioned to allow a surgeon to perform a cut on the patient's bone using the bearing insert for support. A method of manufacturing an orthopaedic surgical instrument is also disclosed.

13 Claims, 11 Drawing Sheets

(56) References Cited

U.S. PATENT DOCUMENTS

| | | |
|---|---|---|
| 5,417,693 A | 5/1995 | Sowden et al. |
| 5,514,140 A | 5/1996 | Lackey |
| 5,690,636 A | 11/1997 | Wildgoose et al. |
| 5,735,856 A | 4/1998 | McCue et al. |
| 5,788,701 A | 8/1998 | McCue |
| 5,951,564 A | 9/1999 | Schroder et al. |
| 5,976,147 A | 11/1999 | LaSalle et al. |
| 6,024,746 A | 2/2000 | Katz |
| 6,059,788 A | 5/2000 | Katz |
| 6,063,091 A | 5/2000 | Lombardo et al. |
| 6,077,270 A | 6/2000 | Katz |
| 6,228,091 B1 | 5/2001 | Lombardo et al. |
| 6,258,095 B1 | 7/2001 | Lombardo et al. |
| 6,294,745 B1 * | 9/2001 | Gruber .................. 174/263 |
| 6,602,258 B1 | 8/2003 | Katz |
| 6,620,168 B1 | 9/2003 | Lombardo et al. |
| 6,673,077 B1 | 1/2004 | Katz |
| 6,740,092 B2 | 5/2004 | Lombardo et al. |
| 2003/0225413 A1 * | 12/2003 | Sanford et al. ................ 606/87 |
| 2005/0124998 A1 | 6/2005 | Coon et al. |
| 2005/0283252 A1 * | 12/2005 | Coon et al. ............... 623/20.35 |
| 2006/0004371 A1 | 1/2006 | Williams, II et al. |
| 2006/0089641 A1 | 4/2006 | Collazo |
| 2006/0111725 A1 | 5/2006 | Biegun |
| 2006/0155380 A1 * | 7/2006 | Clemow et al. ........... 623/20.35 |
| 2007/0010822 A1 | 1/2007 | Zalenski et al. |
| 2007/0208349 A1 | 9/2007 | Bastian et al. |
| 2007/0225710 A1 | 9/2007 | Jahng et al. |
| 2007/0265648 A1 | 11/2007 | Cohen |
| 2008/0221569 A1 | 9/2008 | Moore et al. |
| 2009/0005132 A1 * | 1/2009 | Ogatsu ....................... 455/575.3 |

FOREIGN PATENT DOCUMENTS

| | | |
|---|---|---|
| FR | 2 847 453 A1 | 5/2004 |
| WO | 99/20192 A1 | 4/1999 |
| WO | 2008/035198 A2 | 3/2008 |
| WO | 2008/077927 A2 | 7/2008 |

OTHER PUBLICATIONS

European search report from EP 09 17 8338 dated Jun. 9, 2010. (8 pages).

Tech-Etch Design Guide for Photo Etching Flat Parts, http://www.tech-etch.com/photoetch/flatguide.html (last visited Mar. 4, 2009), (3 pages).

Tech-Etch Design Guide for Photo Etched Formed Parts, http://www.tech-etch.com/photoetch/formedguide.html (last visited Mar. 4, 2009), (3 pages).

MicroEtch Screens from Tech-Etch, http://www.tech-etch.com/photoetch/microscreens.html(last visited Mar. 4, 2009), (2 pages).

The Conard Corporation, Engineering Design Guidelines for PhotoChemical Machining, http://www.conardcorp.com/pdf/DesignGuide.pdf (last visited Mar. 4, 2009), (4 pages).

European search report from EP 09 17 8343 dated Jul. 30, 2010, 7 pages.

Patent Trial and Appeal Board, Decision on Appeal in U.S. Appl. No. 12/345,133, Dec. 21, 2015, 9 pages.

* cited by examiner

ORTHOPAEDIC CUTTING BLOCK HAVING A CHEMICALLY ETCHED METAL INSERT

Cross-reference is made to co-pending U.S. Utility Patent Application Ser. No. 12/345,133 entitled "Orthopaedic Cutting Tool Having a Chemically Etched Metal Insert and Method of Manufacturing" by Jon Edwards, which is assigned to the same assignee as the present application, filed concurrently herewith, and hereby incorporated by reference.

TECHNICAL FIELD

The present disclosure relates generally to orthopaedic surgical instruments, and more particularly to an orthopaedic cutting block having a metallic bearing insert with chemically etched holes.

BACKGROUND

Joint arthroplasty is a well-known surgical procedure by which a diseased and/or damaged natural joint is replaced by a prosthetic joint. Typical artificial joints include knee prostheses, hip prostheses, shoulder prostheses, ankle prostheses, and wrist prostheses, among others. To facilitate the replacement of the natural joint with the prosthesis, orthopaedic surgeons use a variety of orthopaedic surgical instruments such as, for example, saws, drills, reamers, rasps, broaches, cutting blocks, drill guides, milling guides, and other surgical instruments. Typically, orthopaedic surgical instruments are fabricated from metal using traditional manufacturing processes, such as machining, turning, and drilling, and require sterilization between surgical procedures.

SUMMARY

According to one aspect, an orthopaedic cutting block may include a metallic bearing insert and a body molded to the bearing insert. The bearing insert may have a plurality of chemically etched holes and may be configured to support a bone cutting tool. The body may be molded to the bearing insert such that each of the plurality of chemically etched holes is at least partially filled by a portion of the body.

In some embodiments, the bearing insert may have an interface surface which contacts the body and a guide surface opposite the interface surface. The guide surface of the bearing insert may be configured to support a bone cutting tool. Each of the plurality of chemically etched holes in the bearing insert may extend from the interface surface to the guide surface of the bearing insert. The portion of the body which at least partially fills each chemically etched hole may fill at least half the volume of the hole. The bearing insert may be embodied as a bushing, and the guide surface may be configured to support a bone drill bit. The bearing insert may be embodied as a non-captured cutting guide, and the guide surface may be configured to support a bone saw blade. The body may be formed of an injection-molded polymer.

The body of the orthopaedic cutting block may include a bone-facing surface adapted to receive a portion of an anterior side of a patient's tibia, and the bearing insert may be positioned to allow a surgeon to perform a proximal cut on the patient's tibia using the bearing insert for support. The body may include a bone-facing surface adapted to receive a portion of an anterior side of a patient's femur, and the bearing insert may be positioned to allow a surgeon to perform a distal cut on the patient's femur using the bearing insert for support. The body may include a bone-facing surface adapted to contact a resected distal surface of a patient's femur, and the bearing insert may be positioned to allow a surgeon to perform at least one of an anterior cut, a posterior cut, and a chamfer cut on the patient's femur using the bearing insert for support. The body may include a first bone-facing surface adapted to contact a resected anterior surface of a patient's femur and a second bone-facing surface adapted to contact a resected distal surface of the patient's femur; the guide surface of the bearing insert may include a medially-facing section, a laterally-facing section, and a distally-facing section; and the bearing insert may be positioned to allow a surgeon to perform a notch cut on a patient's femur using the bearing insert for support.

In another aspect, an orthopaedic surgical instrument may be embodied as an orthopaedic cutting block. The orthopaedic surgical instrument may include a first metallic bearing insert, a second metallic bearing insert, and a body molded to the first and second bearing inserts. The first bearing insert may have a first plurality of chemically etched holes and may be configured to support a bone cutting tool. The second bearing insert may have a second plurality of chemically etched holes and may be configured to support the bone cutting tool. The body may be molded to the first and second bearing inserts such that each of the first plurality of chemically etched holes and each of the second plurality of chemically etched holes is at least partially filled by a portion of the body.

In some embodiments, the first bearing insert may have an first interface surface which contacts the body and a first guide surface opposite the interface surface. The first guide surface may be configured to support the bone cutting tool. Each of the first plurality of chemically etched holes may extend from the first interface surface to the first guide surface of the first bearing insert. The second bearing insert may have a second interface surface which contacts the body and a second guide surface opposite the interface surface. The second guide surface may be configured to support the bone cutting tool. Each of the second plurality of chemically etched holes may extend from second interface surface to the second guide surface of the second bearing insert. The first bearing insert may oppose the second bearing insert with a gap therebetween. The first and second bearing insert may be embodied as a captured cutting slot configured to support a bone saw blade.

According to another aspect, a method for manufacturing an orthopaedic surgical instrument is disclosed. The method may include chemically etching a plurality of holes into a metallic bearing insert. The method may also include molding a body to the bearing insert to form an orthopaedic cutting block. The method may include chemically etching each of the plurality of holes through the entire thickness of the bearing insert. The method may further include chemically etching a groove into the bearing insert. The method may also further include bending the bearing insert along the groove prior to molding the body to the bearing insert.

In some embodiments, the method may include forming a mask on the bearing insert. The mask may define a plurality of exposed areas on the bearing insert. The method may include placing the bearing insert having the mask in a chemical bath whereby the plurality of exposed areas are chemically etched into the plurality of holes. The method may also include removing the bearing insert having the mask from the chemical bath and removing the mask from the bearing insert. The method may include applying a photoresist material to the bearing insert, selectively exposing portions of the photoresist material to a light source using a patterned photomask, and selectively removing portions of the photoresist material using a developer to define the plurality of exposed areas on the bearing insert.

In some embodiments, the method may include loading the bearing insert into a mold. The bearing insert may contact a wall of the mold. The method may also include injecting a polymer into the mold. The bearing insert may be pressed against the wall of the mold by the polymer. The polymer may at least partially fill the plurality of holes.

BRIEF DESCRIPTION OF THE DRAWINGS

The detailed description particularly refers to the following figures, in which.

DETAILED DESCRIPTION OF THE DRAWINGS

Figure 1:
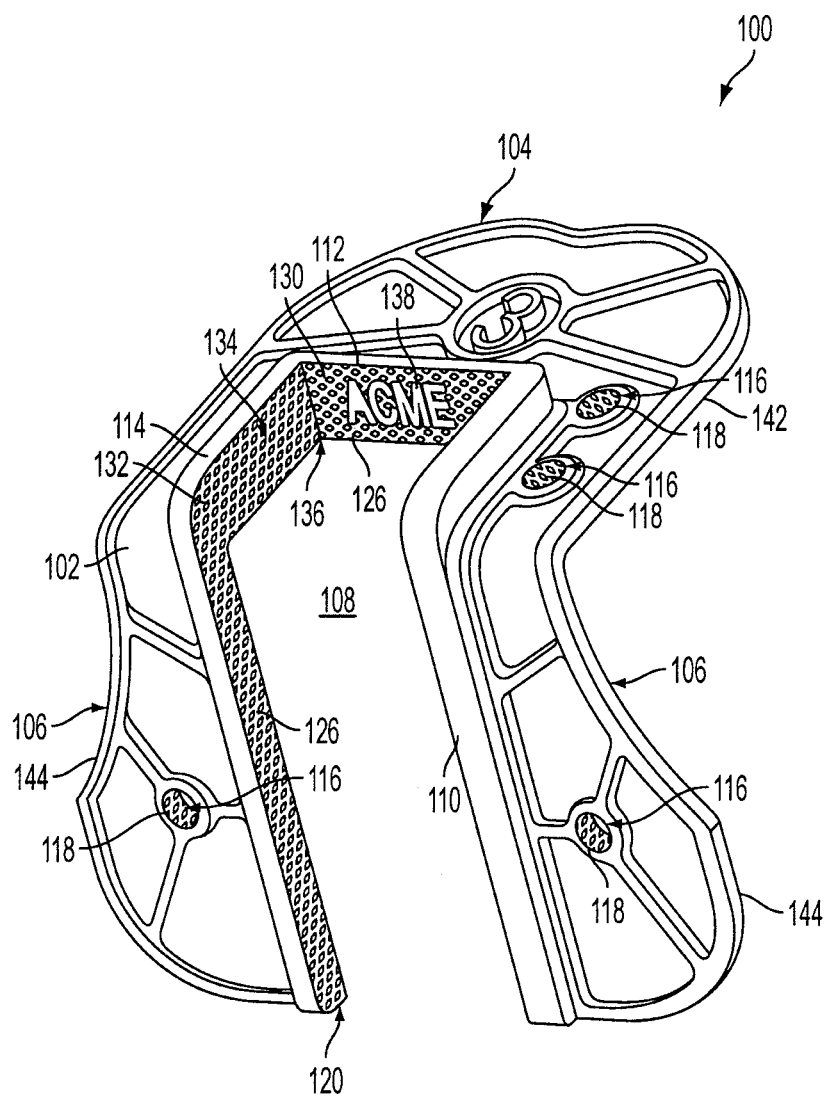
FIG. 1 is a perspective view of one embodiment of an orthopaedic cutting block.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout this disclosure in reference to both the orthopaedic surgical instruments described herein and a patient's natural anatomy. Such terms have well-understood meanings in both the study of anatomy and the field of orthopaedics. Use of such anatomical reference terms in the specification and claims is intended to be consistent with their well-understood meanings unless noted otherwise.

The present disclosure relates generally to orthopaedic surgical instruments which include one or more metallic inserts and a body molded to the metallic inserts. The metallic inserts may be positioned at or near areas of the orthopaedic surgical instrument which are subjected to the greatest forces during use. In some embodiments, the body may be an injection-molded polymer. The metallic inserts include a plurality of chemically etched holes. The chemically etched holes have distinctive structural characteristics and create adhesion between the metallic inserts and the body. The concepts of the present disclosure are applicable both to orthopaedic cutting blocks, which employ metallic bearing inserts, and to orthopaedic cutting tools, which employ metallic cutting inserts.

Referring generally to FIGS. 1-4, one illustrative embodiment of an orthopaedic surgical instrument according to the present disclosure is an orthopaedic cutting block 100 designed to function as a notch guide for use by a surgeon with a surgical bone saw. Similar components are labeled using similar reference numerals in these and all other figures. The orthopaedic cutting block 100 includes several metallic bearing inserts 118, 120 and a body 102 molded to the bearing inserts 118, 120.

Figure 2:
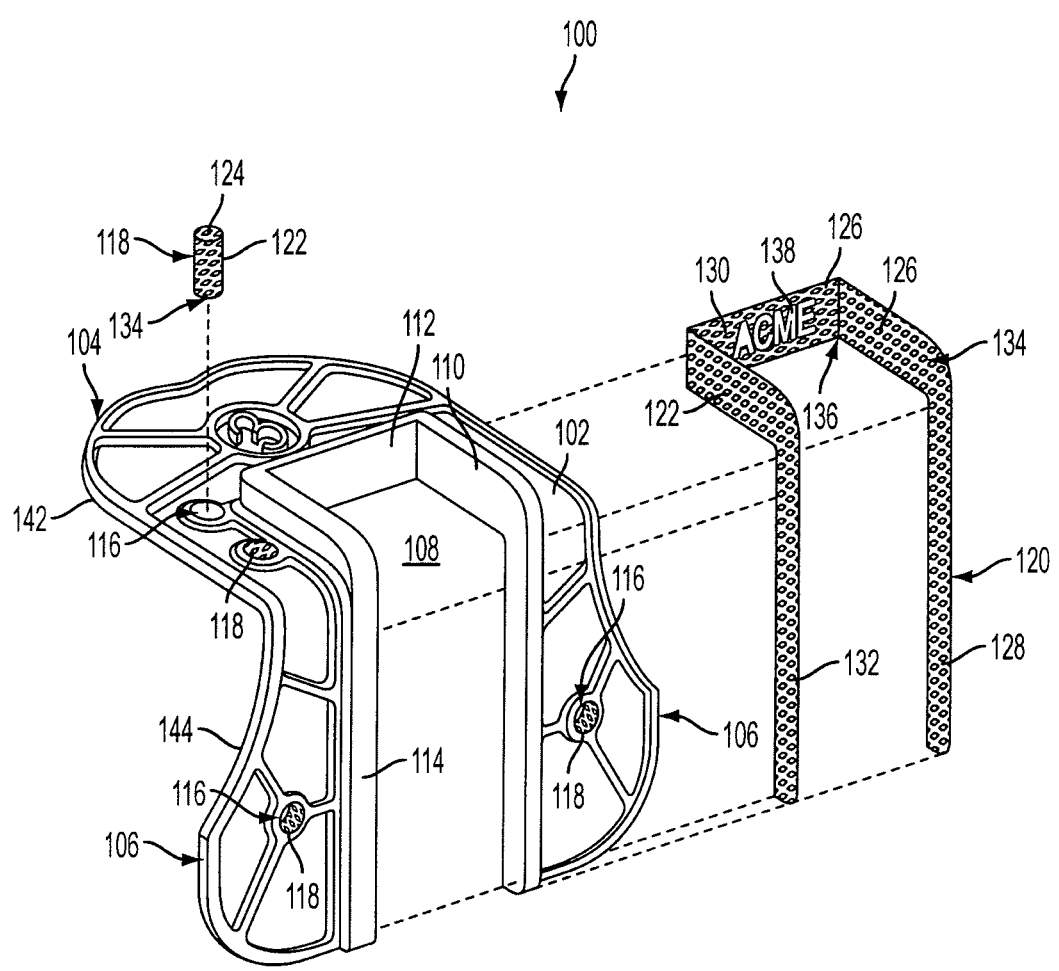
FIG. 2 is a partially exploded, perspective view of the orthopaedic cutting block of FIG. 1.

As shown in FIGS. 1 and 2, the body 102 of orthopaedic cutting block 100 includes an anterior plate 104 and two distal plates 106, generally giving the body 102 the shape of an inverted "L" when viewed from the side and an inverted "U" when viewed from the top. The body 102 further includes a central notch opening 108 defined by a medially-facing wall 110, a distally-facing wall 112, and a laterally-facing wall 114. The anterior plate 104 includes a bone-facing surface 142 which is adapted to contact a resected anterior surface of a patient's femur 10. Each of the two distal plates 106 includes a bone-facing surface 144 adapted to contact a resected distal surface of the patient's femur 10. The body 102 also includes six guide holes 116 (four of which can be seen in each of FIGS. 1 and 2). The number and placement of the guide holes 116 may be varied, and not every guide hole 116 may require a bearing insert 118.

The body 102 may be formed of any material which may be molded to the bearing inserts 118, 120, including, but not limited to, polymers and resins. In some embodiments, the body 102 may be formed of a material which is less capable than the bearing inserts 118, 120 of withstanding external forces, but which is less expensive, lighter, and/or more easily fabricated into complex shapes. The body 102 may be heterogeneous in nature or may be a composite material. In one illustrative embodiment, the body 102 is formed of an injection-molded polymer.

The metallic bearing inserts 118, 120 are generally positioned at or near areas of the orthopaedic cutting block 100 which are subjected to the greatest forces during use. The bearing inserts may be formed of a metal or metallic alloy; in one illustrative embodiment, the bearing inserts 118, 120 be formed of Type 316 or Type 17-4 grade stainless steel. Each bearing insert includes an interface surface 122, which contacts the body (visible in partially exploded view of FIG. 2). Opposite the interface surface 122, each bearing insert also includes a guide surface 124, 126, which is configured to support a bone cutting tool. Each bearing insert 118 functions as a bushing for one of the guide holes 116. Thus, a drill bit or pin passing through one of the guide holes 116 will only, or at least mostly, contact the guide surface 124 of the bearing insert 118 and not the body 102. The bearing insert 120 functions as a non-captured cutting guide for the central notch opening 108. The guide surface 126 includes a medially-facing section 128, a distally-facing section 130, and a laterally-facing section 132, which correspond, respectively, to the medially-facing wall 110, the distally-facing wall 112, and the laterally-facing wall 114 of the body 102. Thus, a bone saw blade 12 (shown in FIG. 4) cutting along the central notch opening 108 will only, or at least mostly, contact the guide surface 126 of the bearing insert 120 and not the body 102. In another embodiment, two or more separate bearing inserts may be used in place of the single, multi-sectioned bearing insert 120.

Each bearing insert 118, 120 includes a plurality of chemically etched holes 134. In one illustrative embodiment, each of the plurality of chemically etched holes 134 extends from the interface surface 122 to the guide surface 124, 126 of the bearing insert 118, 120. The chemically etched holes 134 have distinctive structural characteristics, which will be further described below with reference to FIGS. 3A-D, and create adhesion between the bearing inserts 118, 120 and the body 102. It is contemplated that the chemically etched holes 134 may consist of a variety of shapes and may be arranged in numerous patterns on the surface of the bearing inserts 118, 120. The chemically etched holes 134, in one illustrative embodiment, are circular in shape and approximately 1/50 of an inch in diameter. The bearing inserts 118, 120 may also include other chemically etched features in addition to the chemically etched holes 134. In one illustrative embodiment, bearing insert 120 may further include one or more chemically etched grooves 136 and/or chemically etched indicia 138, such as reference markings, trade names, and product names or numbers, among others.

Figure 3A:
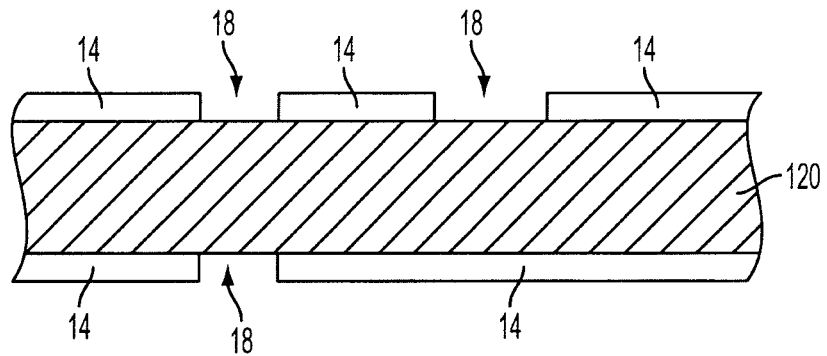
FIG. 3A is a cross sectional view of a portion of a metallic bearing insert prior to chemical etching.

As will be discussed in more detail below, chemically etched holes 134, as well as chemically etched grooves 136, chemically etched indicia 138, and other features, may be formed by placing the metallic bearing inserts 118, 120 in a chemical bath which dissolves exposed metal. The bearing inserts 118, 120 may be selectively etched to form features, such as the plurality of chemically etched holes 134, by forming a mask 14, including a plurality of exposed areas 18, around the bearing inserts 118, 120 prior to placement in the chemical bath, as shown in FIG. 3A. The mask 14 may be formed of any material which is not substantially dissolved by the chemical bath.

Figure 3B:
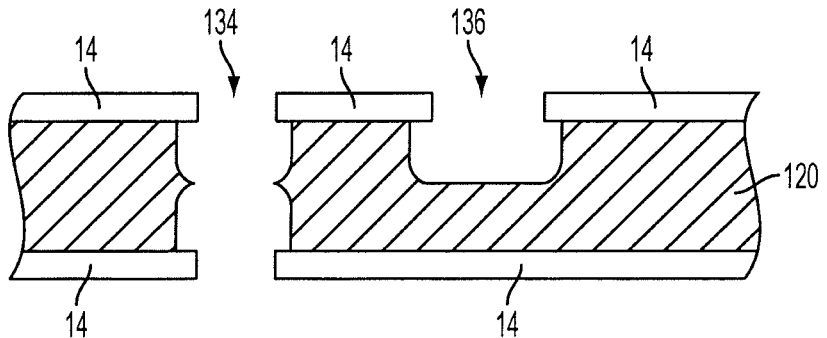
FIG. 3B is a cross sectional view of the portion of the metallic bearing insert of FIG. 3A after chemical etching.

In one illustrative embodiment, the mask 14 is a polymeric photoresist material which is formed around the bearing insert 120, but includes a plurality of exposed areas 18 (see FIG. 3A). A cross-section of the bearing insert 120 of FIG. 3A after removal from the chemical bath but prior to removal of the polymeric photoresist mask 14 is depicted in FIG. 3B. In areas which were exposed to the chemical bath on both sides of the bearing insert 120, the resulting structure is a chemically etched hole 134. The distinctive structural characteristics of the chemically etched hole 134 are due in part to the isotropic nature of the wet, or liquid, chemical etch. As can be seen in FIG. 3B, as the chemical bath dissolves the metal of the bearing insert 120 in a vertical direction, it also dissolves the metal in horizontal directions at approximately 20-25% the rate of the vertical direction. In areas which were exposed to the chemical bath on only one side of the bearing insert 120, the resulting structure is a chemically etched groove 136. The groove 136 may run the entire width of the guide surface 126 of the bearing insert 120. As will be discussed in more detail below, the groove 136 allows for bending of the bearing insert 120—between the medially-facing section 128 and the distally-facing section 130 and between the distally-facing section 130 and the laterally-facing section 132 of the guide surface 126—prior to molding of the body 102 to the bearing insert 120.

Figure 3C:
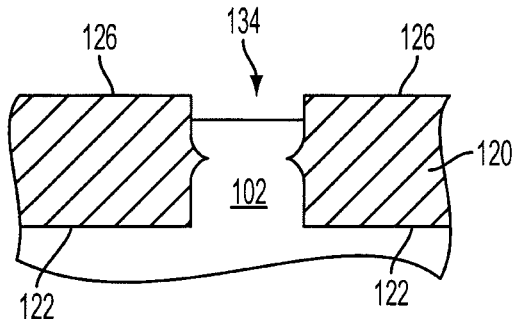
FIG. 3C is a cross sectional view of a portion of a metallic bearing insert after molding with the body, according to one embodiment.

The chemically etched holes 134 create adhesion between the bearing insert 120 and the body 102, as shown in FIG. 3C. As the body 102 is molded to the bearing insert 120, a portion of the body 102 at least partially fills each of the plurality of chemically etched holes 134. After molding, the body 102 contacts the bearing insert 120 at the interface surface 122 and the sidewalls of the chemically etched holes 134, but generally does not contact the guide surface 126, providing a substantially all metallic guide surface 126 configured to support an orthopaedic cutting tool. In one illustrative embodiment, the portion of the body 102 which at least partially fills each chemically etched hole 134 may fill at least half the volume of each hole 134. In another illustrative embodiment, the portion of the body 102 which at least partially fills each chemically etched hole 134 may fill between 70-80% of the volume of each hole 134.

Figure 3D:
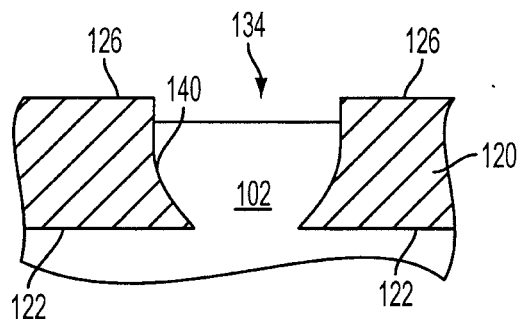
FIG. 3D is a cross sectional view of a portion of a metallic bearing insert after molding with the body, according to another embodiment.

In another illustrative embodiment, shown in FIG. 3D, the chemically etched holes 134 of bearing insert 120 may also be formed by exposing areas on only one side of the bearing insert 120, but allowing the bearing insert 120 to remain in the chemical bath for a longer period of time. This results in a chemically etched hole 134 with its own distinctive structural characteristics, including a tapered sidewall 140. Again, a portion of the body 102 at least partially fills each chemically etched hole 134, but generally does not contact the guide surface 126, providing a substantially all metallic guide surface 126 configured to support an orthopaedic cutting tool. It should be noted that each of the features described with respect to bearing insert 120 and FIGS. 3A-D, may apply equally to the bearing inserts 118 and the chemically etched holes 134 thereof. Furthermore, for these and all other embodiments hereinafter disclosed, while a plurality of the chemically etched holes 134 are at least partially filled by portions of the body 102, it is contemplated that some of the chemically etched holes 134 may not be filled at all.

Figure 4:
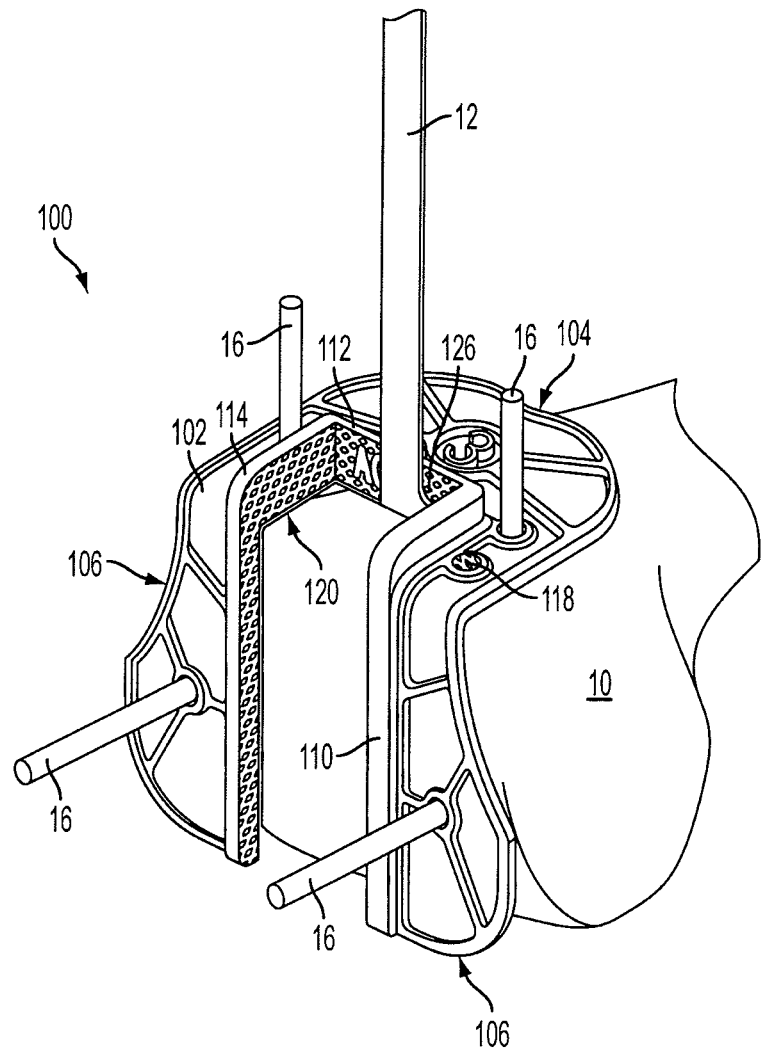
FIG. 4 is a perspective view of the orthopaedic cutting block of FIG. 1 coupled to a bone of a patient.

Placement and use of the orthopaedic cutting block 100 on the distal end of the patient's femur 10 during surgery can be best seen in FIG. 4. Typically, the surgeon will have performed anterior and distal cuts or resections on the patient's femur 10 prior to using the orthopaedic cutting block 100 to perform a notch cut. The orthopaedic cutting block 100 is positioned such that the bone-facing surface 142 of the anterior plate 104 contacts the resected anterior surface of the patient's femur 10 and the bone-facing surfaces 144 of the two distal plates 106 contact the resected distal surface of the patient's femur 10. The orthopaedic cutting block 100 is secured to the patient's femur 10 by the placement of one or more (typically, three or more) surgical pins 16 through the guide holes 116. Once the orthopaedic cutting block 100 is secured, the surgeon may use a typical bone saw having a bone saw blade 12 to perform the notch cut using the bearing insert 120 to support the bone saw blade 12.

Figure 5:
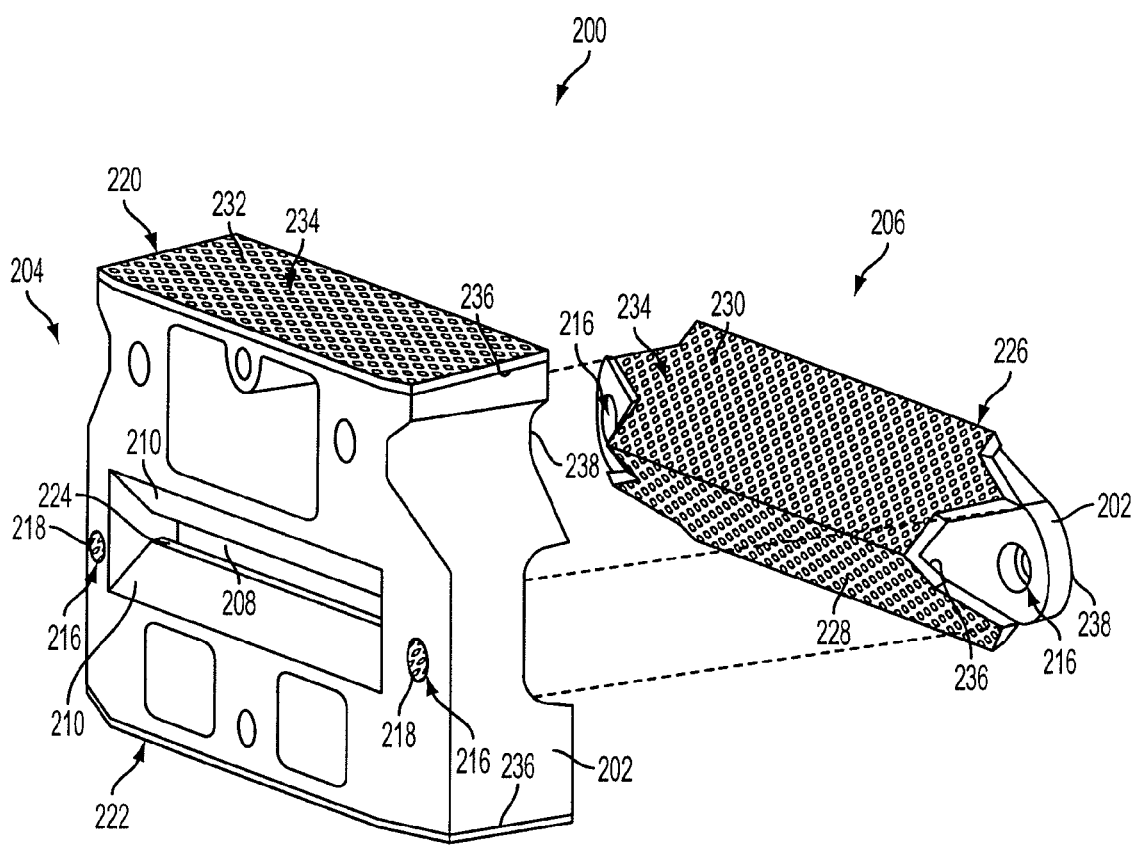
FIG. 5 is a partially exploded, perspective view of another embodiment of an orthopaedic cutting block.
Figure 6:
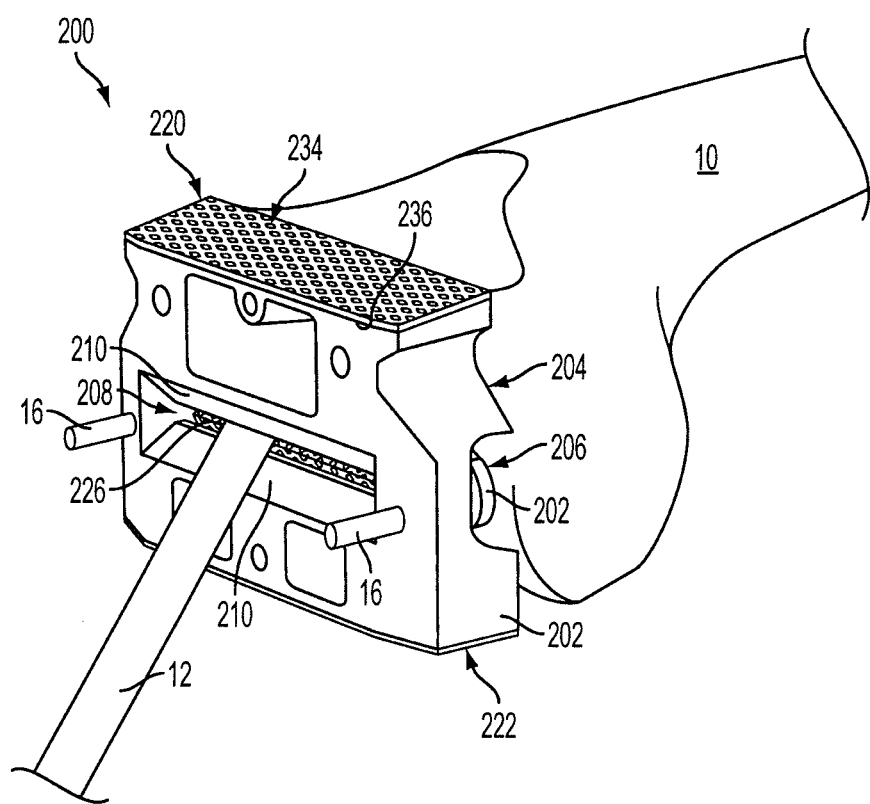
FIG. 6 is a perspective view of the orthopaedic cutting block of FIG. 5 coupled to a bone of a patient.

Referring generally now to FIGS. 5 and 6, another illustrative embodiment of an orthopaedic surgical instrument according to the present disclosure is an orthopaedic cutting block 200 designed to function as an anterior/posterior/chamfer cutting guide, also known in the art as a 4-in-1 cutting block, for use by a surgeon with a surgical bone saw. The orthopaedic cutting block 200 includes several metallic bearing inserts 218-226 and a body 202 molded to the bearing inserts 218-226.

The body 202 of orthopaedic cutting block 200 may be formed of any material which may be molded to the bearing inserts 218-226, such as the materials discussed above with respect to orthopaedic cutting block 100. As shown in FIG. 5, the body 202 includes a pair of body components 204, 206, which when combined give the orthopaedic cutting block 200 a generally cuboid, or rectangular parallelepiped, outer shape. Both the body component 204 and the body component 206 include bone-facing surfaces 238 which are adapted to contact a resected distal surface of a patient's femur 10. The body component 204 further includes an elongated opening 208, generally parallel to an imaginary line drawn between the medial and lateral sides of the body component 204. The elongated opening 208 is defined by a first pair of tapered walls 210 which open toward the distal side of the body component 204 and by a second pair of tapered walls (not shown) which open toward the proximal side of the body component 204. The second pair of tapered walls are designed to receive the body component 206, as indicated in FIG. 5. The body 202 may also include guide holes 216, on both the body component 204 and the body component 206. The number and placement of the guide holes 216 may be varied, and not every guide hole 216 may require a bearing insert 218.

Similar to the bearing inserts 118, 120 of orthopaedic cutting block 100, the bearing inserts 218-226 may be formed of a metal or metallic alloy and are generally positioned at or near areas of the orthopaedic cutting block 200 which are subjected to the greatest forces during use. Each bearing insert includes an interface surface 236, which contacts the body 202. Opposite the interface surface 236, each bearing insert also includes a guide surface 228-232 (and others not shown), which is configured to support a bone cutting tool. Each bearing insert 218 functions as a bushing for one of the guide holes 216. A drill bit or pin passing through one of the guide holes 216 will only, or at least mostly, contact the guide surface of the bearing insert 218 and not the body 202. The bearing insert 220 functions as a non-captured cutting guide for performing an anterior cut on the patient's femur 10. A bone saw blade 12 cutting along the anterior side of the orthopaedic cutting block 200 will only, or at least mostly, contact the guide surface 232 of the bearing insert 220 and not the body 202. Similarly, the bearing insert 222 functions as a non-captured cutting guide for performing a posterior cut on the patient's femur 10. A bone saw blade 12 cutting along the posterior side of the orthopaedic cutting block 200 will only, or at least mostly, contact the guide surface (not shown) of the bearing insert 222 and not the body 202. In another illustrative embodiment, the anterior and posterior cutting guides of orthopaedic cutting block 200 may alternatively be captured cutting slots, similar to those described below, rather than non-captured cutting guides.

The orthopaedic cutting block 200 also includes two captured cutting slots which may support a bone saw blade 12 when performing a pair of chamfer cuts on the patient's femur 10. As discussed above, the body component 204 includes an elongated opening 208, which is in part defined by a second pair of tapered walls which open toward the proximal side of the body component 204. A metallic bearing insert is disposed on each of the second pair of tapered walls: bearing insert 224 on the lower tapered wall, and another bearing insert (not shown) on the upper tapered wall. The body component 206 also has a bearing insert 226. The guide surface of the bearing insert 226 includes a downwardly-facing section 228 and an upwardly-facing section 230. When the body component 204 and the body component 206 are assembled, these bearing inserts form two captured cutting slots. The downwardly-facing section 228 of bearing insert 226 opposes the bearing insert 224 with a gap therebetween to form a downwardly-angled, captured cutting slot. The upwardly-facing section 230 of bearing insert 226 opposes the other bearing insert (not shown) with a gap therebetween to form a upwardly-angled, captured cutting slot. A bone saw blade 12 (shown in FIG. 6) cutting along the elongated opening 108 through one of the captured cutting slots will only, or at least mostly, contact the guide surfaces of the bearing inserts 224, 226 and not the body 202. In another embodiment, two or more separate bearing inserts may be used in place of the multi-sectioned bearing insert 226. In yet another embodiment, any of the captured cutting slots may be formed by a single bearing insert functioning as an elongated bushing, rather than by a pair of opposed bearing inserts.

Each bearing insert 218-226 includes a plurality of chemically etched holes 234 which create adhesion between the bearing inserts 218-226 and the body 202. The chemically etched holes 234 have the same distinctive structural characteristics as the chemically etched holes 134, described above with respect to the orthopaedic cutting block 100 and shown in FIGS. 3A-D. As the body 202 is molded to the bearing inserts 218-226, a portion of the body 202 at least partially fills the chemically etched holes 234. After molding, the body 202 contacts the bearing inserts 218-226 at the interface surfaces 236 and the sidewalls of the chemically etched holes 234, but generally does not contact the guide surfaces, providing substantially all metallic guide surfaces configured to support an orthopaedic cutting tool.

The bearing inserts 218-216 may also include other chemically etched features in addition to the chemically etched holes 234, such as chemically etched grooves or indicia. In one illustrative embodiment, a chemically etched groove may run the entire width of the interface surface 236 of the bearing insert 226. This chemically etched groove would allow for bending of the bearing insert 226 between the downwardly-facing section 228 and the upwardly-facing section 230 prior to molding of the body 202 to the bearing insert 226.

Placement and use of the orthopaedic cutting block 200 on the distal end of the patient's femur 10 during surgery can be best seen in FIG. 6. Typically, the surgeon will have performed a distal cut or resection on the patient's femur 10 prior to using the orthopaedic cutting block 200 to perform one or more of an anterior cut, a posterior cut, or a chamfer cut. The orthopaedic cutting block 200 is positioned such that the bone-facing surfaces 238 of the body component 204 and of the body component 206 rest on the resected distal surface of the patient's femur 10. The orthopaedic cutting block 200 is secured to the patient's femur 10 by the placement of one or more (typically, two) surgical pins 16 through the guide holes 216 of the body component 204 and the body component 206. Once the orthopaedic cutting block 200 is secured, the surgeon may use a typical bone saw having a bone saw blade 12 to perform an anterior resection using the bearing insert 220 for support (shown completed), to perform a posterior resection using the bearing insert 222 for support (also shown completed), or to perform two chamfer resections using the captured cutting slots, as shown in FIG. 6. When the surgeon uses one of the captured cutting slots, the bone saw blade 12 is guided by the bearing inserts 224, 226, and avoids contact with the body 202, including the first pair of tapered walls 210.

It should be noted that an orthopaedic surgical instrument according to the present disclosure may be embodied as additional or different orthopaedic cutting blocks, other than those discussed above. By way of illustrative example, a distal femoral cutting block might include an injection-molded body and a metallic bearing insert having a plurality of chemically etched holes and positioned to allow a surgeon to perform a distal cut on a patient's femur using the bearing insert for support. As a further illustrative example, a proximal tibial cutting block might include an injection-molded body and a metallic bearing insert having a plurality of chemically etched holes and positioned to allow a surgeon to perform a proximal cut on a patient's tibia using the bearing insert for support. Indeed, it is believed that there are few, if any, orthopaedic cutting blocks to which the principles of the present disclosure would not be applicable.

Figure 7:
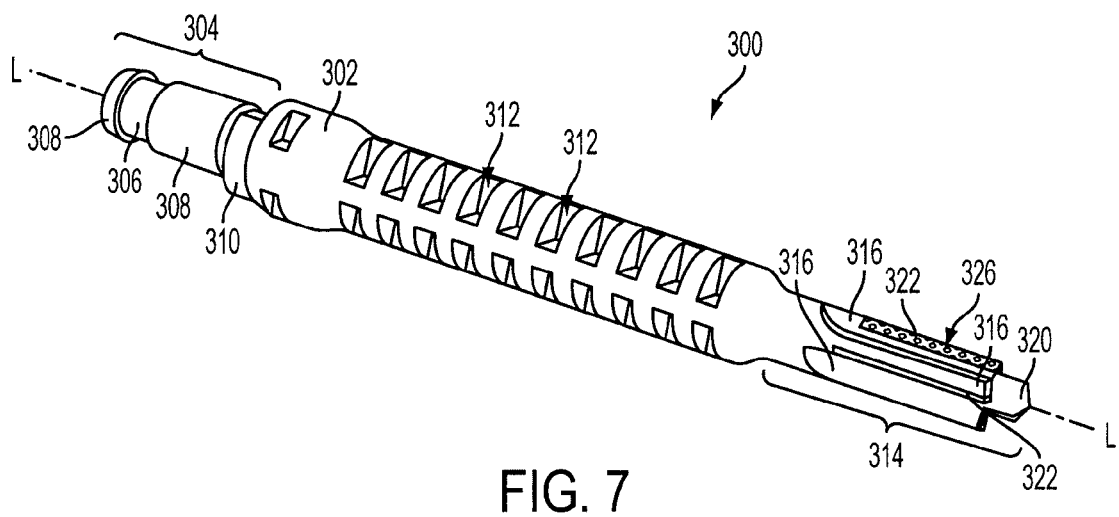
FIG. 7 is a perspective view of one embodiment of an orthopaedic cutting tool.
Figure 8:
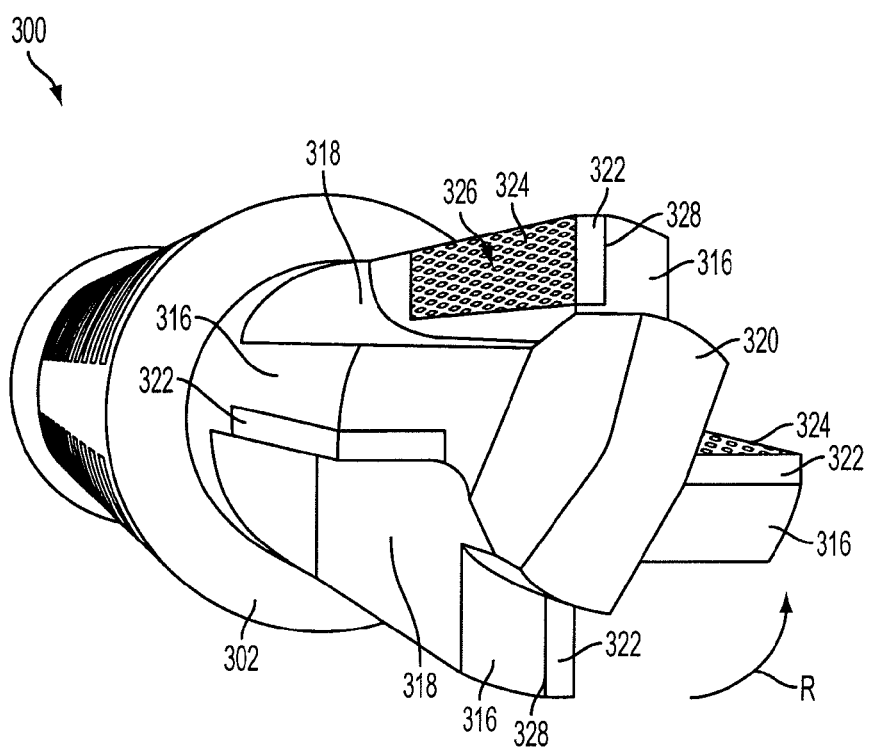
FIG. 8 is a perspective view of the orthopaedic cutting tool of FIG. 7.

Referring generally now to FIGS. 7-8, another illustrative embodiment of an orthopaedic surgical instrument according to the present disclosure is an orthopaedic cutting tool 300 designed to function as drill bit for use by a surgeon with a surgical bone drill. The orthopaedic cutting tool 300 includes a plurality of metallic cutting inserts 322 and a body 302 molded to the plurality of cutting inserts 322.

The body 302 of orthopaedic cutting tool 300 may be formed of any material which may be molded to the plurality of cutting inserts 322, such as the materials discussed above with respect to orthopaedic cutting block 100. In one illustrative embodiment, the body 302 of the orthopaedic cutting tool 300 is formed of an injection-molded polymer. As shown in FIG. 7, the body 302 is generally cylindrical in shape, having a longitudinal axis L. The body 302 may be a generally solid cylinder or may optionally include voids 312, such as those shown in FIG. 7, in order to decrease the amount of material used to create the body 302. The body 302 includes a cutting segment 314, on which the plurality of cutting inserts 322 are disposed. The body 302 may also include an integrally formed coupling feature 304, at the end opposite the cutting segment 314 along the longitudinal axis L. The coupling feature 304 may include narrower sections 306, wider sections 308, and/or non-cylindrically-shaped sections 310 to allow a typical surgical bone drill (not shown) to couple to the orthopaedic cutting tool 300.

The cutting segment 314 of the body 302 of orthopaedic cutting tool 300, which is shown in detail in FIG. 8, includes a plurality of cutting flutes 316. The plurality of cutting flutes 316 are arranged radially outward around the longitudinal axis L of the orthopaedic cutting tool 300. A channel 318 is situated between each pair of adjacent cutting flutes 316 to allow bone fragments removed by the orthopaedic cutting tool 300 to exit the patient's bone. In operation, a surgeon may couple the orthopaedic cutting tool 300 to the surgical bone drill to cause rotation of the cutting segment 314 about the longitudinal axis L in the direction of arrow R indicated in FIG. 8. The cutting segment 314 of the body 302 may also include a pointed tip 320 to assist in guiding the orthopaedic cutting tool 300.

Similar to the bearing inserts 118, 120 of orthopaedic cutting block 100, the cutting inserts 322 of the orthopaedic cutting tool 300 may be formed of a metal or metallic alloy. Each of the plurality of cutting inserts 322 is disposed on one of the plurality of cutting flutes 316 and is generally aligned with a leading edge of the cutting flute 316 on which it is disposed. It is also contemplated that some, but not all, of the plurality of cutting flutes 316 may have a cutting insert 322 disposed thereon. Each cutting insert 322 includes an interface surface 328, which contacts the body 302. Opposite the interface surface 328, each cutting insert 322 also includes a work surface 324 which is configured to contact and remove portions of the patient's bone during rotation of the orthopaedic cutting tool 300 in the direction of the arrow R.

Each cutting insert 322 includes a plurality of chemically etched holes 326 which create adhesion between the plurality of cutting inserts 322 and the body 302. The chemically etched holes 326 have the same distinctive structural characteristics as the chemically etched holes 134, described above with respect to orthopaedic cutting block 100 and shown in FIGS. 3A-D. As the body 302 is molded to the cutting inserts 322, a portion of the body 302 at least partially fills each of the plurality of chemically etched holes 326. After molding, the body 302 contacts the plurality of cutting inserts 322 at the interface surfaces 328 and the sidewalls of the chemically etched holes 326, but generally does not contact the work surfaces 324, providing substantially all metallic work surfaces 324 configured to remove portions of a patient's bone.

Figure 9:
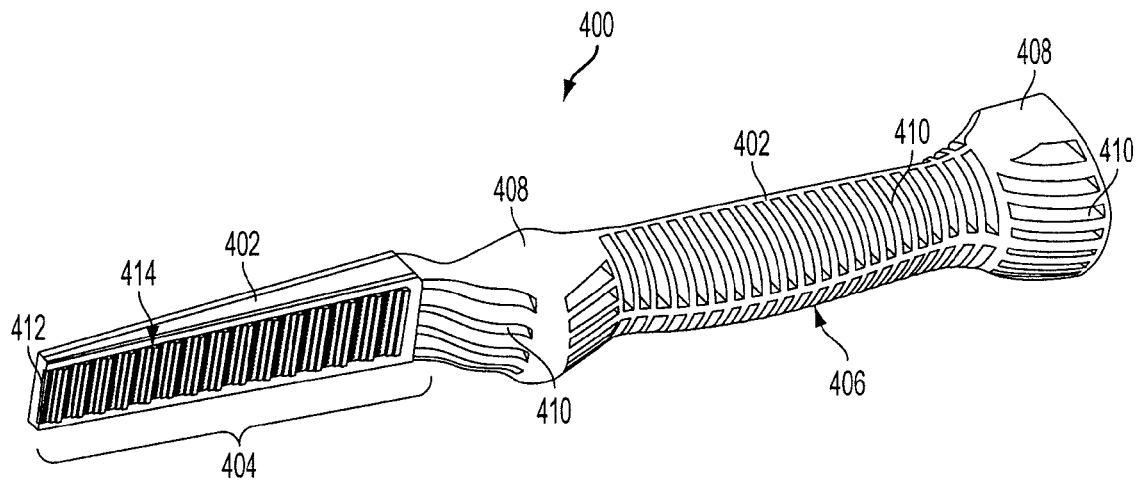
FIG. 9 is a perspective view of another embodiment of an orthopaedic cutting tool.
Figure 10:
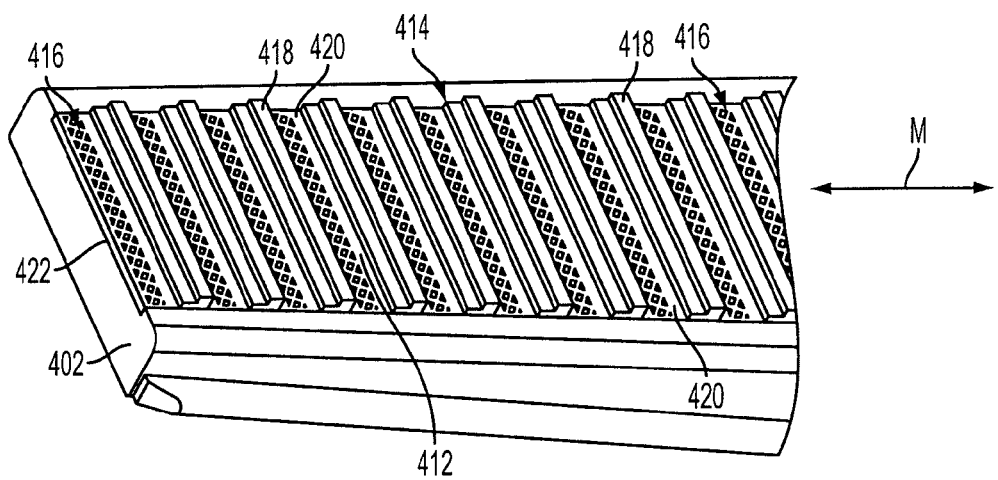
FIG. 10 is a perspective view of a portion of the orthopaedic cutting tool of FIG. 9.

Referring generally now to FIGS. 9-10, another illustrative embodiment of an orthopaedic surgical instrument according to the present disclosure is an orthopaedic cutting tool 400 designed to function as a rasp for use by a surgeon in manually removing portions of a patient's bone. The orthopaedic cutting tool 400 includes a metallic cutting insert 412 and a body 402 molded to the cutting insert 412.

The body 402 of orthopaedic cutting tool 400 may be formed of any material which may be molded to the metallic cutting insert 412, such as the materials discussed above with respect to orthopaedic cutting block 100. In one illustrative embodiment, the body 402 of the orthopaedic cutting tool 400 is formed of an injection-molded polymer. As shown in FIG. 9, the body 402 includes a cutting segment 404, on which the cutting insert 412 is disposed. The body 402 also includes an integrally formed handle 406, at the end opposite the cutting segment 404, which may be gripped by the surgeon during use. The handle 404 may be ergonomically shaped and the body 402 may also include bulges 408 near the ends of the handle 406 so that the orthopaedic cutting tool 400 may be more easily grasped by the surgeon. The body 402 may be generally solid or may optionally include voids 410, such as those shown in FIG. 9, in order to decrease the amount of material used to create the body 402.

The cutting segment 404 of the body 402 of orthopaedic cutting tool 400, which is shown in detail in FIG. 10, is molded to the cutting insert 412. Similar to the bearing inserts 118, 120 of orthopaedic cutting block 100, the cutting insert 412 of the orthopaedic cutting tool 400 may be formed of a metal or metallic alloy. The cutting insert 412 includes an interface surface 422, which contacts the body 402. Opposite the interface surface 422, the cutting insert 412 also includes a work surface 414, which is configured to remove portions of the patient's bone during motion of the orthopaedic cutting tool 400 in the direction of the arrow M indicated in FIG. 10. In operation, a surgeon may grip the orthopaedic cutting tool 400 at the handle 406, place the work surface 414 in contact with the patient's bone, and move to the orthopaedic cutting tool 400 reciprocally in the direction of arrow M.

The cutting insert 412 includes a plurality of chemically etched holes 416 which create adhesion between the cutting insert 412 and the body 402. The chemically etched holes 416 have the same distinctive structural characteristics as the chemically etched holes 134, described above with respect to orthopaedic cutting block 100 and shown in FIGS. 3A-D. As the body 402 is molded to the cutting insert 412, a portion of the body 402 at least partially fills each of the plurality of chemically etched holes 416. After molding, the body 402 contacts the cutting insert 412 at the interface surface 422 and the sidewalls of the chemically etched holes 416, but generally does not contact the work surface 414, providing substantially all metallic work surface 414 configured to remove portions of a patient's bone.

To assist in the removal of portions of the patient's bone, the work surface 414 of the cutting insert 412 includes a plurality of chemically etched cutting teeth 418. In one illustrative embodiment, shown in FIG. 10, the plurality of chemically etched cutting teeth 418 are etched into the work surface 414 of the cutting insert 412 to have a cross-section consisting of two steps with sharp, generally right-angled edges configured to remove portions of the patient's bone. The chemically etched cutting teeth 418 span the entire width of the cutting insert 412 and are arranged perpendicularly to the length of the cutting insert 412. The work surface 414 also includes a relief surface 420 situated between each pair of adjacent cutting teeth 412. In this embodiment, the plurality of chemically etched holes 416 extend from the interface surface 422 to the relief surfaces 420 of the cutting insert 412. It is contemplated that the work surface 414 may take other forms, such as a single relief surface 420 with a plurality of chemically etched cutting teeth 418 raised above the relief surface 420 and arranged in various patterns. Various configurations of the work surface 414 may be formed by selectively exposing areas on one or both sides of the cutting insert 412 to the chemical bath in a single or multi-step etching process, as discussed below.

It should be noted that an orthopaedic surgical instrument according to the present disclosure may be embodied as additional or different orthopaedic cutting tools, in addition to those discussed above. By way of illustrative example, an orthopaedic surgical reamer might include an injection-molded body and a plurality of metallic cutting inserts having chemically etched holes and disposed at the cutting edges of the instrument to allow a surgeon to ream an intramedullary canal of a long bone using the cutting inserts. As a further illustrative example, an orthopaedic surgical broach might include an injection-molded body and a metallic cutting insert having chemically etched holes and cutting teeth to allow a surgeon to prepare a femur for placement of a femoral component during a hip arthroplasty. Indeed, it is believed that there are few, if any, orthopaedic cutting tools to which the principles of the present disclosure would not be applicable.

Figure 11:
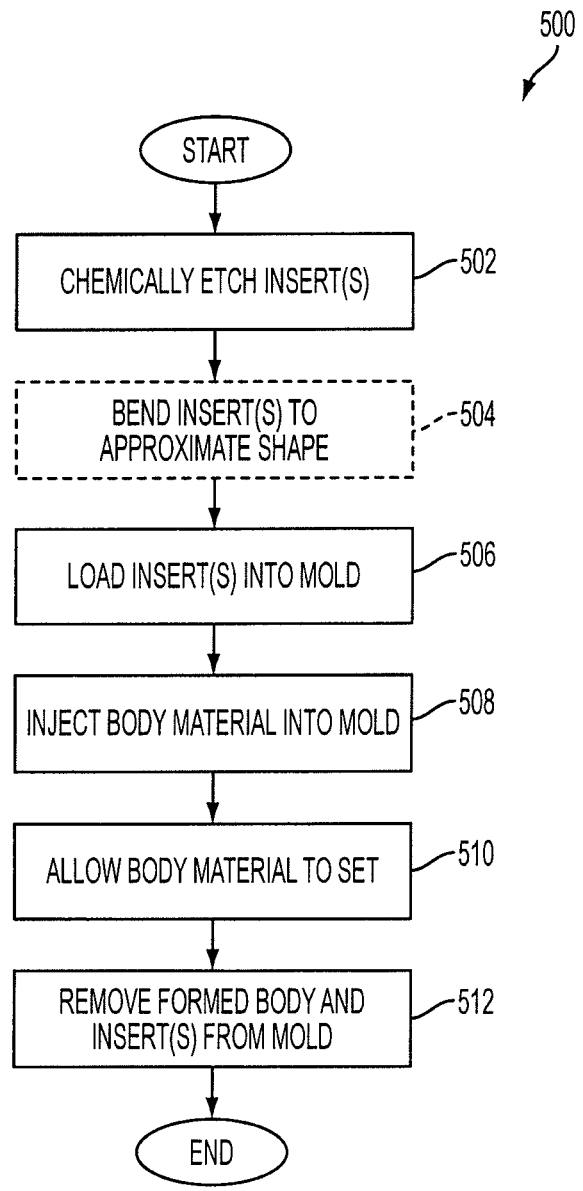
FIG. 11 is a simplified flow diagram of a method for manufacturing an orthopaedic surgical instrument.
Figure 12:
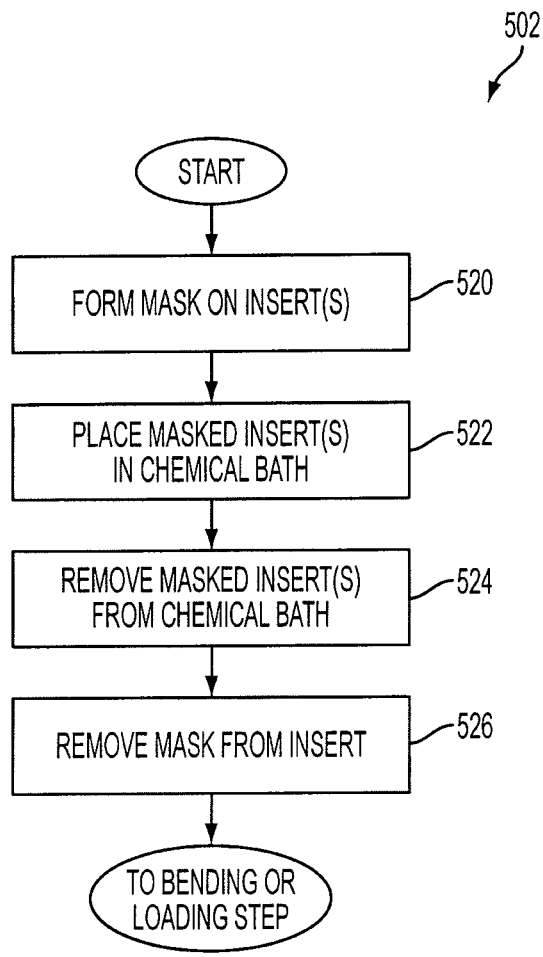
FIG. 12 is a simplified flow diagram of a method for chemically etching a metallic insert.
Figure 13:
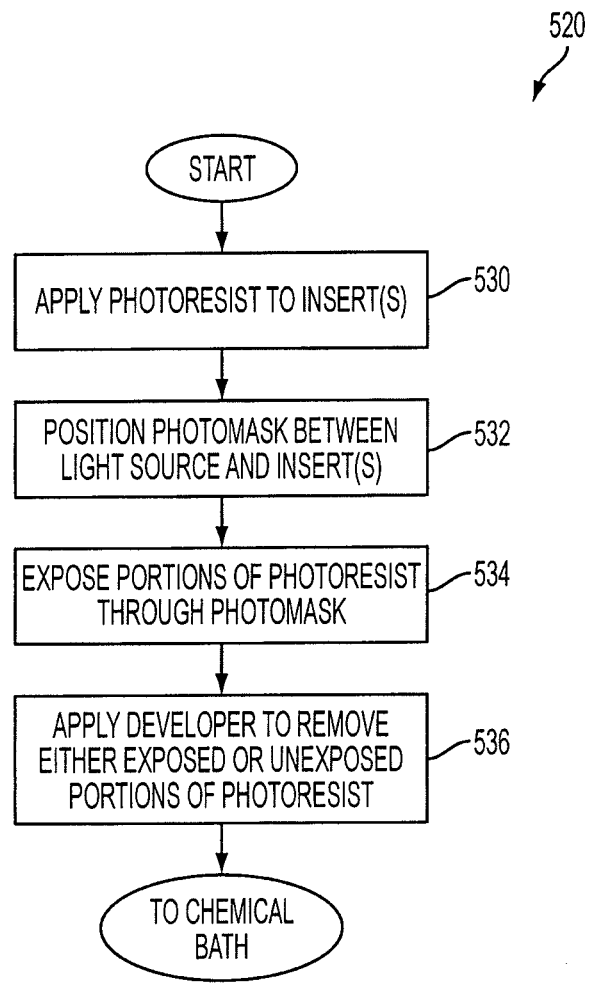
FIG. 13 is a simplified flow diagram of a method for forming a mask on a metallic insert.

Referring generally now to FIGS. 11-13, an illustrative embodiment of a method for manufacturing an orthopaedic surgical instrument according to the present disclosure is illustrated as a series of simplified flow diagrams. The manufacturing process 500 may be used to fabricate an orthopaedic cutting block, in which case one or more metallic bearing inserts would be used, or may be used to fabricate an orthopaedic cutting tool, in which case one or more metallic cutting inserts would be used. In describing the illustrative embodiments of this method, the term "insert(s)," without a modifier, shall be used to signify either one or more metallic bearing inserts or one or more metallic cutting inserts. The manufacturing process 500 includes a number of process steps 502-512, as shown in FIG. 11.

The manufacturing process 500 begins with process step 502, in which the insert or inserts to be used in forming the orthopaedic surgical instrument are chemically etched to include a plurality of holes and any other desired features. The chemical etching may be performed with any chemical which dissolves metal, including, but not limited to, hydrochloric acid, ammonium persulfate, and ferric chloride. As will be described in more detail below with respect to FIG. 12, process step 502 will include chemically etching a plurality of holes into the insert in every embodiment, but may also include etching additional features, including grooves, indicia, cutting teeth, and/or relief surfaces, in some illustrative embodiments. Process step 502 may involve a single chemical etch or may involve multiple chemical etches, as needed.

After process step 502, the manufacturing process 500 optionally proceeds to process step 504, in which the insert or inserts may be bent into the approximate shape needed for the orthopaedic surgical instrument, if necessary. Process step 504 may be used when a single insert will occupy multiple planes in the finished surgical instrument. For instance, bearing insert 120 in orthopaedic surgical block 100 and bearing insert 226 in orthopaedic surgical block 200 is bent prior to process step 506. Bending of the insert may be facilitated by one or more chemically etched grooves, such as the groove 136 described above and shown in FIG. 3B. The insert need only be bent to its approximate shape, as process step 508 will further form the insert to the correct shape, as discussed below.

After process step 502, or optional process step 504, the manufacturing process 500 proceeds to process step 506, in which the insert or inserts are loaded into a mold. In one illustrative embodiment, the insert is loaded into the mold such that a guide surface (if a bearing insert) or a work surface (if a cutting insert) contacts a wall or walls of the mold. The inserts may be held in place in the mold in a number of ways, including gravitational, magnetic, or other forces.

After process step 506, the manufacturing process 500 proceeds to process step 508, in which the body material is injected into the mold. As discussed above, the body material may be any substance which may be molded to the inserts, including, but not limited to, polymers and resins. In some illustrative embodiments, the body material may be a substance which is less expensive, lighter, and/or more easily fabricated into complex shapes than the metallic inserts. Process step 508 may include heating the body material to make the material suitable for injecting into the mold. In process step 508, the force of the body material injected into the mold presses the inserts to the walls of the mold, further shaping inserts which were bent during optional process step 504 into the proper shape. A portion of the body material may at least partially fill the plurality of holes in the insert which were chemically etched in process step 502. In some embodiments, the body material will substantially fill all of the holes in the insert. In other embodiments, many or most of the holes will be filled, while others will be left unfilled.

After process step 508, the manufacturing process 500 proceeds to process step 510, in which the body material is allowed to set into its final, rigid form. Process step 510 may involve allowing the heated body material to cool to a temperature lower than its temperature when injected into the mold. In some illustrative embodiments, the body material will reach the wall of the mold during injection in process step 508 and be flush with the guide surface (if a bearing insert) or the work surface (if a cutting insert). During process step 510, the body material may retract slightly while setting, resulting in the portion of the body only partially filling the hole, as shown in the cross-sections of FIGS. 3C and 3D.

After process step 510, the manufacturing process 500 proceeds to process step 512, in which a formed body and insert(s) are removed from the mold. At this point, another insert or set of inserts, which have been chemically etched according to process step 502, may be loaded into the mold according to process step 506 and the process may be repeated. It is also contemplated that the manufacturing process 500 may include additional process steps. For instance, in some embodiments, after the formed body and insert(s) are removed from the mold in process step 512, additional assembly of the orthopaedic surgical instrument may be required.

One illustrative embodiment of process step 502 of the manufacturing process 500 is shown in detail in FIG. 12 as a chemical etching sub-process consisting of process steps 520-526. In every embodiment, the chemical etching sub-process 502 will include chemically etching a plurality of holes into an insert. In some illustrative embodiments, the chemical etching sub-process 502 may also include etching additional features, including grooves, indicia, cutting teeth, and/or relief surfaces into the insert. These features may be chemically etched into the insert along with the holes simultaneously, that is during a single iteration of the chemical etching sub-process 502. Alternatively, the process steps 520-526 may be repeated, as needed, to form the appropriate chemically etched features before returning to manufacturing process 500.

The chemical etching sub-process 502 begins with process step 520, in which a mask is formed on the insert or inserts. As shown in the cross-section of FIG. 3A, the mask 14 is formed around the metal to be chemically etched into the inserts, but includes a plurality of exposed areas 18. The mask may be formed from any material which is not substantially dissolved by the chemical bath of process step 522. As will be described in more detail below with respect to FIG. 13, one illustrative embodiment of process step 520 may include forming a layer of polymeric photoresist around the inserts to act as a mask during etching. The mask may be formed on one side, both sides, or neither side of the insert at various positions, depending on the desired feature at that position.

After process step 520, the chemical etching sub-process 502 proceeds to process step 522, in which the insert or inserts having the mask or masks are placed in a chemical bath. The chemical bath may include any chemicals which dissolve the metal of the inserts, but do not substantially dissolve the mask material, including, but not limited to, hydrochloric acid, ammonium persulfate, and ferric chloride. During process step 522, the chemical bath selectively attacks and dissolves the metal of the inserts at the plurality of exposed areas 18 (FIG. 3A). As a wet, or liquid, chemical etch is isotropic in nature, the chemical bath dissolves the metal of the inserts in horizontal directions, as well as the vertical direction, resulting in the structures shown in FIG. 3B-D. Etching occurs in the horizontal directions at approximately 20-25% the rate of the vertical direction.

After process step 522, the chemical etching sub-process 502 proceeds to process step 524, in which the insert or inserts having the mask or masks are removed from the chemical bath after a predetermined amount of time. In addition to the pattern of the mask applied in process step 520, the form of the inserts will also be determined by the amount of time elapsed between process steps 522 and 524. If the chemical etch is allowed to proceed for approximately the time required to dissolve half the thickness of an insert, areas which were exposed to the chemical bath on both sides of the insert will result in a hole which extends through the entire thickness of the insert, while areas which were exposed to the chemical bath on only one side of the insert will result in a groove, as shown in FIG. 3B. If the chemical etch is allowed to proceed for approximately the time required to dissolve the entire thickness of an insert, areas which were exposed to the chemical bath on only one side of the insert will result in a hole with a tapered sidewall, similar in structure to that shown in FIG. 3D. It is contemplated that holes and other features of various other cross-sections may formed by chemically etching a particular distance into the insert from one side using a first mask, then repeating the chemical etching sub-process 502 using a second mask and chemically etching the remainder of the thickness of the insert from the opposite side.

After process step 524, the chemical etching sub-process 502 proceeds to process step 526, in which the mask applied in process step 520 is removed from the insert or inserts. At this point, the chemically etching sub-process 502 may be repeated, if necessary, or the manufacturing process 500 may proceed to one of process step 504 or process step 506. It should also be noted that the chemical etching sub-process 502 may be applied to one insert at a time, or multiple inserts may be chemically etched in parallel. In one illustrative embodiment, a large metallic sheet of appropriate thickness, containing multiple rows and columns of inserts, may proceed through the chemical etching sub-process 502. The mask formed in process step 520 may include an outline around all or substantially all of each insert, such that the inserts either fall out of the sheet during chemical etching or may be easily removed afterward.

One illustrative embodiment of the process step 520 of the chemical etching sub-process 502 is shown in detail in FIG. 13 as a mask forming sub-process consisting of process steps 530-536. The mask forming sub-process 520 is a photolithography process in which one or more patterned photomasks are used to form a light-sensitive material into a mask having a plurality of exposed areas on the insert or inserts.

The mask forming sub-process 520 begins with process step 530, in which a photoresist material is applied to substantially cover the exterior of the insert or inserts. The photoresist material is a polymeric substance which changes its structure in response to exposure to an ultraviolet ("UV") light source. The coating of photoresist material may be a positive photoresist, which becomes more soluble when exposed to UV light. Alternatively, the coating of photoresist material may be a negative photoresist, which becomes polymerized and less soluble when exposed to UV light. The coating of photoresist material may be applied in numerous ways, including high-velocity spin coating. The photoresist material may also need to be heated slightly before becoming light-sensitive.

After process step 530, the mask forming sub-process 520 proceeds to process step 532, in which a first patterned photomask is positioned between a UV light source and a first side of the insert covered in photoresist material. The first patterned photomask includes both translucent and opaque portions. If a positive photoresist is used in process step 530, the translucent portions of the photomask will correspond to the plurality of exposed areas 18 in the mask 14 (FIG. 3A). If a negative photoresist is used in process step 530, the opaque portions of the photomask will correspond to the plurality of exposed areas 18 in the mask 14 (FIG. 3A).

After process step 532, the mask forming sub-process 520 proceeds to process step 534, in which the UV light source is turned on and areas of the photoresist material are selectively exposed to the light source through the translucent portions of the first patterned photomask. In response, the chemical structure of the exposed areas of photoresist will change, becoming more or less soluble depending on the type of photoresist used. Process steps 530 and 532 may be repeated using a second photomask and a second side of the insert, if needed. Alternatively, the first and second photomasks may be positioned at the same time, each with its own light source, and the first and second sides of the insert may be exposed simultaneously.

After process step 534, the mask forming sub-process 520 proceeds to process step 536, in which a developer is applied to the insert to selectively remove areas of the photoresist material to define the plurality of exposed areas on the insert. The developer is a chemical solution which dissolves the more soluble areas of the photoresist material, but not the less soluble areas. The developer may be applied in numerous ways, including high-velocity spin coating. After developing, the remaining photoresist material may again need to be heated to harden into a mask that can withstand the chemical bath. At this point, the mask forming sub-process 520 is complete, and the chemically etching sub-process 502 may proceed to process step 522.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the apparatus and method described herein. It will be noted that alternative embodiments of the apparatus and methods of the present disclosure may not include all of the features described yet still benefit from at least some of the advantages of such features. Those of ordinary skill in the art may readily devise their own implementations of the apparatus and methods that incorporate one or more of the features of the present invention and fall within the spirit and scope of the present disclosure as defined by the appended claims.

Cross-reference is made to co-pending U.S. Utility patent application Ser. No. 12/345,133 entitled "Orthopaedic Cutting Tool Having a Chemically Etched Metal Insert and Method of Manufacturing" by Jon Edwards, which is assigned to the same assignee as the present application, filed concurrently herewith, and hereby incorporated by reference.

The invention claimed is:

1. An orthopaedic cutting block, comprising:
   a metallic bearing insert having a plurality of chemically etched holes, the bearing insert being configured to support a bone cutting tool; and
   a body molded to the bearing insert such that each of the plurality of chemically etched holes is at least partially filled by a portion of the body.

2. The orthopaedic cutting block of claim 1, wherein:
   the bearing insert has (i) an interface surface which contacts the body, and (ii) a guide surface opposite the interface surface, the guide surface configured to support the bone cutting tool; and
   each of the plurality of chemically etched holes extends from the interface surface to the guide surface of the bearing insert.

3. The orthopaedic cutting block of claim 2, wherein the portion of the body which at least partially fills each chemically etched hole fills at least half the volume of the hole.

4. The orthopaedic cutting block of claim 2, wherein the bearing insert functions as a bushing, the guide surface being configured to support a bone drill bit.

5. The orthopaedic cutting block of claim 2, wherein the bearing insert functions as a non-captured cutting guide, the guide surface being configured to support a bone saw blade.

6. The orthopaedic cutting block of claim 1, wherein:
   the body includes a bone-facing surface adapted to receive a portion of an anterior side of a patient's tibia; and
   the bearing insert is positioned to allow a surgeon to perform a proximal cut on the patient's tibia using the bearing insert for support.

7. The orthopaedic cutting block of claim 1, wherein:
   the body includes a bone-facing surface adapted to receive a portion of an anterior side of a patient's femur; and
   the bearing insert is positioned to allow a surgeon to perform a distal cut on the patient's femur using the bearing insert for support.

8. The orthopaedic cutting block of claim 1, wherein:
   the body includes a bone-facing surface adapted to contact a resected distal surface of a patient's femur; and
   the bearing insert is positioned to allow a surgeon to perform at least one of an anterior cut, a posterior cut, and a chamfer cut on the patient's femur using the bearing insert for support.

9. The orthopaedic cutting block of claim 1, wherein:
   the body includes a first bone-facing surface adapted to contact a resected anterior surface of a patient's femur and a second bone-facing surface adapted to contact a resected distal surface of the patient's femur;
   the guide surface of the bearing insert comprises a medially-facing section, a laterally-facing section, and a distally-facing section; and
   the bearing insert is positioned to allow a surgeon to perform a notch cut on a patient's femur using the bearing insert for support.

10. The orthopaedic cutting block of claim 1, wherein the body comprises an injection-molded polymer.

11. An orthopaedic surgical instrument, comprising:
    an orthopaedic cutting block having (i) a first metallic bearing insert having a first plurality of chemically etched holes, the first bearing insert being configured to support a bone cutting tool, (ii) a second metallic bearing insert having a second plurality of chemically etched holes, the second bearing insert being configured to support the bone cutting tool, and (iii) a body molded to the first and second bearing inserts such that each of first plurality of chemically etched holes and each of the second plurality of chemically etched holes is at least partially filled by a portion of the body.

12. The orthopaedic surgical instrument of claim 11, wherein:
    the first bearing insert has (i) a first interface surface which contacts the body, and (ii) a first guide surface opposite the first interface surface, the first guide surface configured to support the bone cutting tool;
    each of the first plurality of chemically etched holes extends from the first interface surface to the second guide surface of the first bearing insert;
    the second bearing insert has (i) a second interface surface which contacts the body, and (ii) a second guide surface opposite the second interface surface, the second guide surface configured to support the bone cutting tool; and
    each of the second plurality of chemically etched holes extends from the second interface surface to the second guide surface of the second bearing insert.

13. The orthopaedic surgical instrument of claim 11, wherein the first bearing insert opposes the second bearing insert with a gap therebetween, the first and second bearing insert comprising a captured cutting slot configured to support a bone saw blade.

* * * * *